(12) United States Patent
Makino (10) Patent No.: US 10,939,801 B2
(45) Date of Patent: Mar. 9, 2021

(54) ELECTRONIC ENDOSCOPE SYSTEM

(71) Applicant: HOYA CORPORATION, Tokyo (JP)

(72) Inventor: Takao Makino, Tokyo (JP)

(73) Assignee: HOYA CORPORATION, Tokyo (JP)

(\*) Notice: Subject to any disclaimer, the term of this patent is extended or adjusted under 35 U.S.C. 154(b) by 0 days.

(21) Appl. No.: 16/489,532

(22) PCT Filed: Mar. 26, 2018

(86) PCT No.: PCT/JP2018/012099
§ 371 (c)(1),
(2) Date: Aug. 28, 2019

(87) PCT Pub. No.: WO2018/181156
PCT Pub. Date: Oct. 4, 2018

(65) Prior Publication Data
US 2020/0008652 A1    Jan. 9, 2020

(30) Foreign Application Priority Data

Mar. 31, 2017 (JP) .............................. JP2017-070407

(51) Int. Cl.
*A61B 1/00* (2006.01)
*A61B 1/005* (2006.01)
(Continued)

(52) U.S. Cl.
CPC ........ *A61B 1/00009* (2013.01); *A61B 1/0051* (2013.01); *A61B 1/045* (2013.01);
(Continued)

(58) Field of Classification Search
CPC ...... H04N 7/18; A61B 1/00009; A61B 1/045; A61B 1/0638; A61B 1/0684; A61B 1/0051; A61B 1/0646; G02B 23/24
(Continued)

(56) References Cited

U.S. PATENT DOCUMENTS 10,420,457 B2   9/2019  Chiba
10,426,325 B2   10/2019 Chiba
(Continued)

FOREIGN PATENT DOCUMENTS

CN    105701792 A    6/2016
CN    106388756 A    2/2017
(Continued)

OTHER PUBLICATIONS

International Search Report issued in WIPO Patent Application No. PCT/JP2018/012099, dated May 22, 2018.

*Primary Examiner* — Loi H Tran (74) *Attorney, Agent, or Firm* — Greenblum & Bernstein, P.L.C.

(57) ABSTRACT

An electronic endoscope system includes: an electronic endoscope including an image sensor that images a living tissue; a processor that performs image processing on an image obtained by imaging the living tissue; and a display that displays the image on which image processing has been performed. The processor includes: a feature amount calculation unit that calculates, as a feature amount, a ratio between differences of values of two color signals out of a plurality of color signals of each of pixels of the image from a reference value; and an image enhancement processing unit that enhances the image by determining a degree of increase or decrease of at least one of the values of the two color signals on the basis of the calculated ratio so as to perform enhancement processing on the image.

11 Claims, 8 Drawing Sheets

(51) Int. Cl.
*A61B 1/045* (2006.01)
*A61B 1/06* (2006.01)
*G02B 23/24* (2006.01)
*H04N 7/18* (2006.01)

(52) U.S. Cl.
CPC .......... *A61B 1/0684* (2013.01); *A61B 1/0638* (2013.01); *A61B 1/0646* (2013.01); *G02B 23/24* (2013.01); *H04N 7/18* (2013.01)

(58) Field of Classification Search
USPC ......................................................... 348/65
See application file for complete search history.

(56) References Cited

U.S. PATENT DOCUMENTS

| | | | |
|---|---|---|---|
| 10,441,147 B2 | 10/2019 | Obara | |
| 2005/0267374 A1 | 12/2005 | Yokomise et al. | |
| 2007/0269087 A1 | 11/2007 | Ikemoto | |
| 2014/0152706 A1* | 6/2014 | Park | H04N 1/6052 345/690 |
| 2015/0054965 A1* | 2/2015 | Sudo | H04N 5/23293 348/169 |
| 2016/0171718 A1* | 6/2016 | Kuramoto | A61B 5/0084 382/128 |
| 2016/0189635 A1* | 6/2016 | Lee | G09G 3/3233 345/690 |
| 2017/0032539 A1 | 2/2017 | Kuramoto | |
| 2017/0208309 A1* | 7/2017 | Oike | H04N 9/315 |
| 2017/0273543 A1 | 9/2017 | Makino | |
| 2017/0280971 A1 | 10/2017 | Makino | |
| 2018/0049679 A1 | 2/2018 | Chiba | |
| 2018/0158180 A1 | 6/2018 | Yokouchi | |
| 2019/0008361 A1* | 1/2019 | Imai | H04N 7/18 |
| 2019/0008362 A1* | 1/2019 | Kamon | G06T 7/0012 |
| 2019/0014294 A1* | 1/2019 | Chae | H04N 9/3182 |
| 2019/0158707 A1 | 5/2019 | Yokouchi | |
| 2019/0282064 A1 | 9/2019 | Makino | |
| 2019/0282065 A1 | 9/2019 | Makino | |
| 2019/0307332 A1 | 10/2019 | Chiba | |
| 2019/0335978 A1 | 11/2019 | Chiba | |

FOREIGN PATENT DOCUMENTS

| | | | |
|---|---|---|---|
| CN | 107072509 A | 8/2017 | |
| CN | 107529957 A | 1/2018 | |
| EP | 3123927 A1 | 2/2017 | |
| JP | 01-113020 A | 5/1989 | |
| JP | 06-245899 A | 9/1994 | |
| JP | 2006-266750 A | 10/2006 | |
| JP | 2007-306974 A | 11/2007 | |
| JP | 2009-106424 A | 5/2009 | |
| JP | 5006759 B2 | 6/2012 | |
| JP | 2016-107003 A | 6/2016 | |
| JP | 2017-023620 A | 2/2017 | |
| WO | WO-2017026540 A1 * | 2/2017 | G06T 5/001 |
| WO | 2017/057680 A1 | 4/2017 | |
| WO | 2017/150071 A1 | 9/2017 | |

* cited by examiner

ELECTRONIC ENDOSCOPE SYSTEM

TECHNICAL FIELD

The present technology relates to an electronic endoscope system that performs image enhancement processing.

BACKGROUND ART

Electronic endoscopes are used for observation or treatment of living tissue in the human body. In many cases, images of living tissue imaged by an electronic endoscope and displayed on a display are images on which image processing has been performed to be able to achieve higher visibility in a whole or a portion of living tissue of interest than other portions. The image processing includes contrast enhancement processing, full image brightening processing, tint change processing, and enhancement processing including shade conversion to expand the number of shades in a predetermined shade level range.

For example, a tone curve for changing and outputting the shade level of an input image is set in enhancement processing in many cases. Such a tone curve is stored and held in advance, and the tone curve stored and held is retrieved in the enhancement processing to perform enhancement processing on an image obtained by the electronic endoscope. Accordingly, the type of enhancement processing to be performed is determined by the tone curve.

For example, a known technology of an electronic endoscope device is capable of obtaining an image in which a blood vessel is sufficiently enhanced even with the use of white light (Patent Literature 1).

This technology includes a RGB converter for converting image signals into RGB signals, an R signal amplifier for increasing or decreasing R signals of RGB signals with a fixed gain, and a GB signal amplifier that performs nonlinear increase or decrease of G signals and B signals of the RGB signals. At this time, gains in the R signal amplifier and the GB signal amplifier are stored as unique values for each of sites to be observed, and the gain is selected on the basis of the site to be observed.

CITATION LIST

Patent Literature

Patent Literature 1: JP 5006759 B2

SUMMARY OF TECHNOLOGY

Technical Problem

In the above technology, the gain selection in the R signal amplifier and the GB signal amplifier is performed by selecting a preset tone curve. That is, the above-described technology sets, in color space formed by RGB color signals, a tone curve separately for color signals of a portion having characteristic tint such as blood vessels among an image of entirely reddish living tissue, for example, G signal or B signal, and for the other color signals, for example, the R signal, and then widens a difference between the colon signal values of the characteristic portion to be enhanced to perform image enhancement processing.

This enhancement processing, however, has a disadvantage. That is, it would be possible, in a portion where the color signal value is within a predetermined range, to perform enhancement of increasing the difference between the values by enlarging an increase amount of the value for enhancement as the color signal value increases. However, in a portion where the color signal value is out of the predetermined range, the difference between the color signal values would be compressed, leading to generation of lossy image for this portion, which might be indistinguishable on a display image.

In addition, in the enhancement processing using tone curve, shade conversion is applied to the shade level of the color signal using a lookup table, and the shade level after shade conversion is output. For this reason, in order to use a plurality of tone curves, there is a need to prepare a plurality of lookup tables for each of three color signals of RGB. Moreover, in the above-described technology, since the gain is selected on the basis of the site to be observed, there is a need to prepare a lookup table for each of the sites. For this reason, the processor that performs image processing needs a large amount of memory for storing and holding the lookup table, and this can be a problem in implementation of a simple device configuration.

In particular, in a case where there is an image of a characteristic portion having a color component different from that of the other portions, and this characteristic portion is difficult to distinguish because of its position in a dark part, it is preferable to perform enhancement processing to enable distinction of this characteristic portion and enable suppressing a stat where the number of shades of the image the other portions is compressed and indistinguishable. In other words, it is preferable to change, on one image, degree of enhancement processing between a characteristic portion having a characteristic color component in the image and portions other than the characteristic portion in the image.

In consideration of the above, the present technology aims to provide an electronic endoscope system capable of changing the degree of enhancement processing between a characteristic portion having a characteristic color component in the image and portions other than the characteristic portion in the image without using a plurality of lookup tables.

Solution to Problem

One aspect of the present technology is an electronic endoscope system. The electronic endoscope system includes:

an electronic endoscope including an image sensor that images a living tissue;

a processor that performs image processing on an image obtained by imaging living tissue; and a display that displays the image on which image processing has been performed, in which the processor includes: a feature amount calculation unit that calculates, as a feature amount, a ratio between differences of values of two color signals out of a plurality of color signals of each of pixels of the image from respective reference values for the two color signals; and an image enhancement processing unit that enhances the image by determining a degree of increase or decrease of at least one of the values of the two color signals on the basis of the calculated ratio so as to perform enhancement processing on the image.

The two color signals are a first color signal and a second color signal, the ratio is a ratio of a second difference of a value of the second color signal from one of the reference values corresponding to the second color signal with respect to a first difference of a value of the first color signal from one of the reference values corresponding to the first color signal, and the image enhancement processing unit preferably performs at least one of enlarging an increase amount of the value of the second color signal or enlarging a decrease amount of the value of the first color signal, as the ratio becomes greater.

The reference values include a first reference value for the first color signal and a second reference value for the second color signal, and each of the first reference value and the second reference value is preferably a changeable value.

When changing the reference values, it is preferable that the feature amount calculation unit sets change amounts of the first reference value and the second reference value to be different from each other.

It is preferable that the feature amount calculation unit sets the reference values in accordance with distribution of the two color signals on whole of the image or luminance information regarding the whole of the image.

It is preferable that the image is one image out of a moving image of a living tissue, the feature amount calculation unit and the image enhancement processing unit sequentially process each of images of the moving image, and the luminance information used for setting the reference value is luminance information of whole of a last image preceding the image on which enhancement processing is performed in time series, out of the moving image.

It is preferable that the feature amount calculation unit sets the reference values to input values received from an operator viewing the image displayed on the display, and that the age enhancement processing unit uses the set reference value to perform enhancement processing on the image.

It is preferable that the color signals are KGB color signals, and that the ratio includes one of a ratio of a difference of a value of a G signal from one of the reference values corresponding to the G signal with respect to a difference of a value of an R signal from one of the reference values corresponding to the R signal, or a ratio of a difference of a value of a B signal from one of the reference values corresponding to the B signal with respect to the difference of the value of the R signal from one of the reference values corresponding to the R signal.

Advantageous Effects of Technology

According to the above-described electronic endoscope system, it is possible to change the degree of enhancement processing between a characteristic portion having a characteristic color component in an image and portions other than the characteristic portion in the image without using a plurality of lookup tables.

DESCRIPTION OF EMBODIMENTS (Configuration of Electronic Endoscope System)

Figure 1:
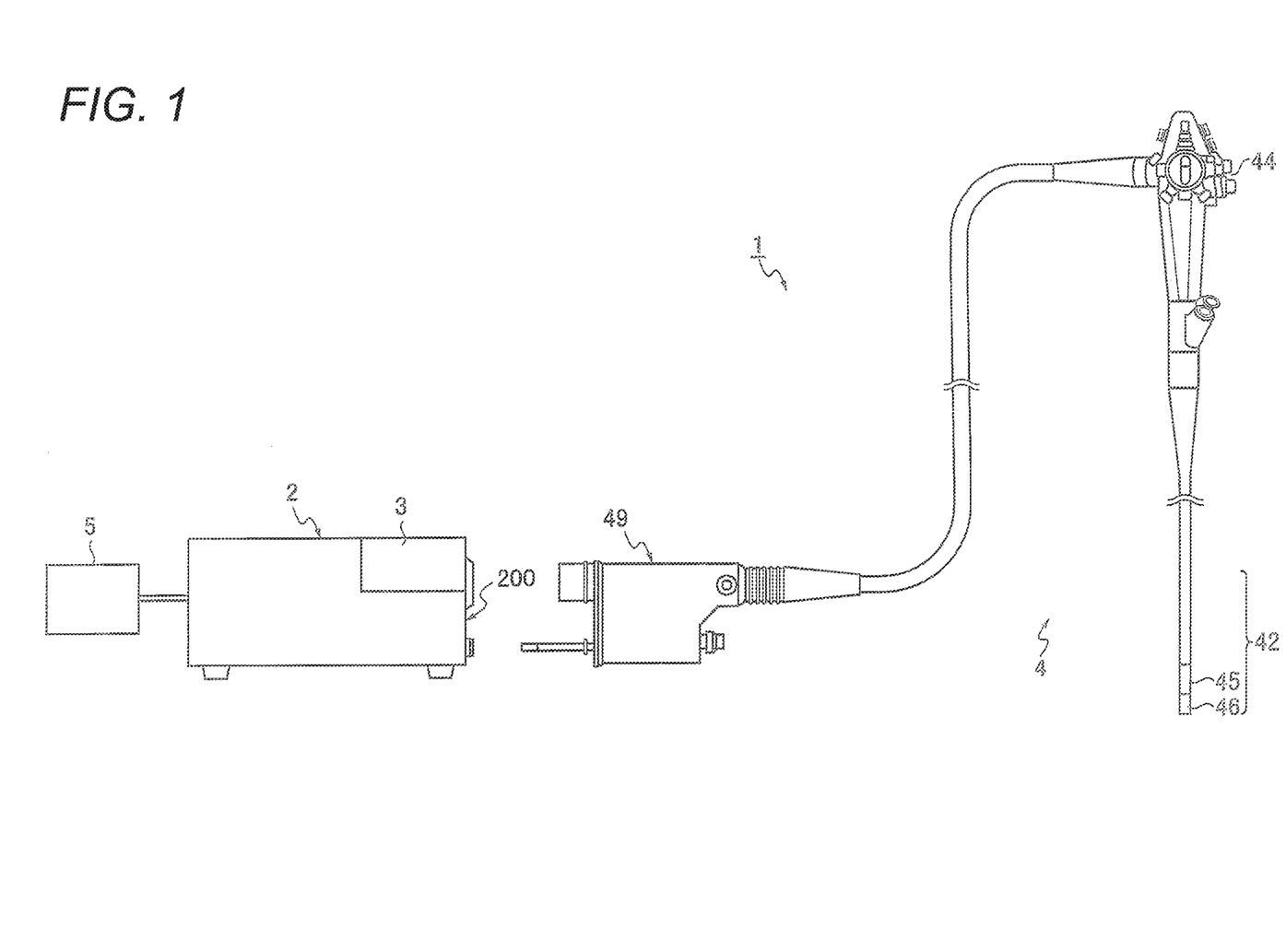
FIG. 1 is an external perspective view of an example of an electronic endoscope system of the present embodiment.
Figure 2:
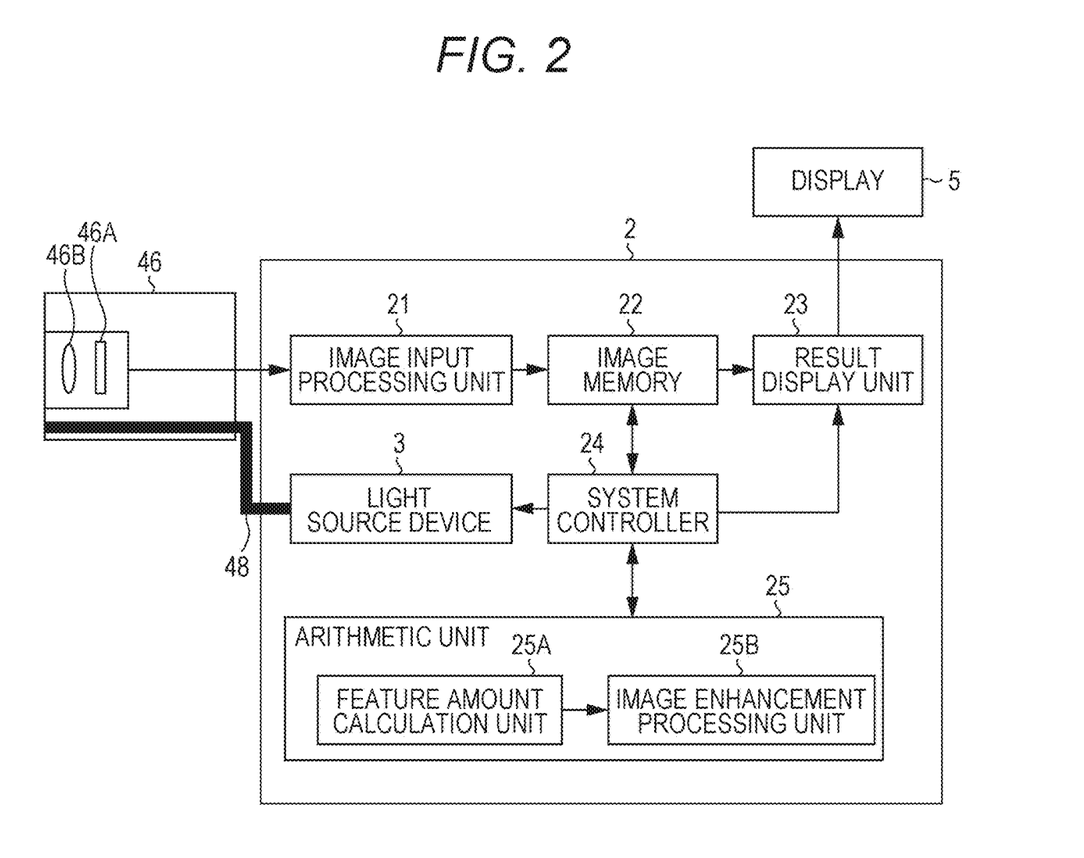
FIG. 2 is a block diagram of an example of the electronic endoscope system of the present embodiment.

Hereinafter, an electronic endoscope system of the present embodiment will be described in detail. FIG. 1 is an external perspective view of an electronic endoscope system 1 of the present embodiment. FIG. 2 is a block diagram illustrating a main configuration of the electronic endoscope system 1.

The electronic endoscope system 1 mainly includes a processor 2, a light source device 3, an electronic endoscope 4, and a display 5. Each of the light source device 3, the electronic endoscope 4, and the display 5 is connected to the processor 2. Although the light source device 3 and the processor 2 are separately configured, the light source device 3 may be provided in the processor 2.

The light source device 3 emits white light or light of a plurality of wavelength bands. The light source device 3 includes, for example, a white light source such as a high intensity lamp including a light emitting diode (LED) light source, a halogen lamp, and a metal halide lamp. The light source device 3 may have a configuration in which a rotating plate with a plurality of optical filters is rotated to switch the optical filters passing through an optical path of the emitted light from the white light source so as to sequentially output the light filtered by each of the optical filters. In this case, the light source device 3 includes members (not illustrated) such as a lamp power driver, a light source, a condenser lens, a filter turret, a motor, and a motor driver, for example. The light source device 3 may include a plurality of semiconductor light emitting elements such as light emitting diodes or laser diodes that emit light of various wavelength bands.

As illustrated in FIG. 1, the electronic endoscope 4 includes, on its distal end, an insertion portion 42 that has flexibility and is to be inserted into the human body. The insertion portion 42 includes, in the vicinity of the distal end thereof, a bending portion 45 that is bendable in response to remote control from a hand operation unit 44 coupled to a proximal end of the insertion portion 42. The bending mechanism of the bending portion 45 is a known mechanism incorporated in a general endoscope. The bending structure is provided to bend the bending portion 45 by pulling an operation wire interlocked with rotational operation of a bending operation knob provided on the hand operation unit 44. The distal end of the bending portion 45 is further coupled to a distal end portion 46 equipped with an image sensor 46A (refer to FIG. 2). The direction of the distal end portion 46 can be changed together with the bending operation of the bending portion 45 by the rotational operation of the bending operation knob, and this directional change allows an imaging region of the electronic endoscope 4 to move.

The electronic endoscope 4 includes a light guide 48 (refer to FIG. 2) disposed substantially over the entire length from the connector unit 49 to the distal end portion 46. The light guide 48 is an optical fiber bundle, and guides irradiation light supplied from the light source device 3 up to the distal end portion 46 of the electronic endoscope 4.

The distal end portion 46 of the electronic endoscope 4 includes: a light distribution lens (not illustrated) provided in front of the distal end of the light guide 48; an objective lens 46B (refer to FIG. 2) for forming an image of a living tissue; the image sensor 46A (refer to FIG. 2) for receiving the formed image; and an amplifier (not illustrated) that amplifies an image signal output from the image sensor 46A.

The light distribution lens is disposed to face a distal end surface of the light guide 48, and allows the irradiation light emitted from the distal end surface of the light guide 48 to diverge and illuminate the living tissue as the subject.

The objective lens 46B collects scattered light or reflected light from the living tissue to form an image of the subject on a light receiving surface of the image sensor 46A.

Examples of the suitably used image sensor 46A include a CCD image sensor or a CMOS image sensor.

An imaging signal output from the image sensor 46A is amplified by an amplifier (not illustrated) and then sequentially transmitted to the connector unit 49.

The connector unit 49 is connected to the processor 2. The connector unit 49 may include a circuit having the following functions. For example, the connector unit 49 may include a circuit that supplies a drive signal to the image sensor 46A to drive the image sensor 46A, converts an analog signal output from the image sensor 46A into a digital signal, and transmits the signal to the processor 2 as a signal of a captured image. In addition, the circuit may include a function of accessing a memory (not illustrated) provided in the connector unit 49, reading out unique information of the electronic endoscope 4 and outputting the information to the processor 2.

The processor 2 is a device that further processes the signal of the captured image obtained by imaging the living tissue by the image sensor 46A of the electronic endoscope and supplies the processed signal to the display 5.

The processor 2 includes another connector unit (not illustrated) for connecting to the electronic endoscope 4. Mechanical connection of the connector unit and the connector unit 49 enables electronic connection between the electronic endoscope 4 and the processor 2, as well as enabling optical connection between the light source device 3 and the electronic endoscope 4.

The processor 2 includes an image input processing unit 21, an image memory 22, a result display unit 23, a system controller 24, and an arithmetic unit 25. FIG. 2 illustrates a configuration including an exchangeable light source device 3 within a housing in which the processor 2 is provided.

The system controller 24 manages and controls operation of the image input processing unit 21, the image memory 22, the result display unit 23, and the arithmetic unit 25, and controls operation of the light source device 3 and the electronic endoscope 4. The processor 2 includes a memory (not illustrated) that stores information and data, in addition to the image memory 22.

The image input processing unit 21 is a unit that performs predetermined signal processing such as color correction and matrix operation on a signal of a living tissue image. Video signals on which signal processing has been performed are transmitted pixel by pixel to the image memory 22 being a frame memory as a captured image and temporarily stored.

The image stored in the image memory 22 is retrieved for enhancement processing, and is transmitted to the arithmetic unit 25 via the system controller 24 in accordance with an instruction from the system controller 24. The processing in the arithmetic unit 25 will be described below.

The image processed by the arithmetic unit 25 is transmitted to the image memory 22 again and stored.

The result display unit 23 retrieves the image stored in the image memory 22, performs signal processing ($\gamma$ correction, or the like) on the signal of the image to generate an image signal for monitor display, and then converts the generated image signal into a predetermined video format signal. The converted video format signal is output to the display 5. With this configuration, an image of the living tissue is displayed as a moving image on a display screen of the display 5.

In such a processor 2, the arithmetic unit 25 performs image enhancement processing on an image of a living tissue. As illustrated in FIG. 2, the arithmetic unit 25 includes a feature amount calculation unit 25A and an image enhancement processing unit 25B.

The feature amount calculation unit 25A calculates a ratio between differences of values of two color signals out of a plurality of color signals of the image from reference values.

Specifically, the feature amount calculation unit 25A calculates the ratio between the differences of values of two signals, for example, the R signal and the Ci signal, out of the RGB signals of each o pixels constituting the image, from the reference values. The feature amount calculation unit 25A may use the R signal and the B signal as the two signals and may calculate the ratio between the differences of the values of the R signal and the B signal from the reference values.

Figure 3A:
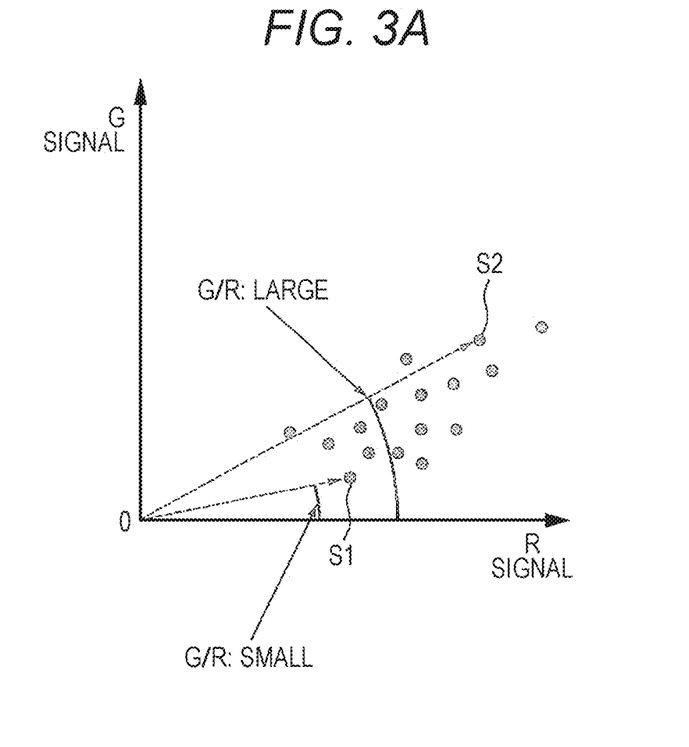
FIGS. 3A and 3B are diagrams illustrating an example of enhancement processing performed by the electronic endoscope system of the present embodiment.
Figure 3B:
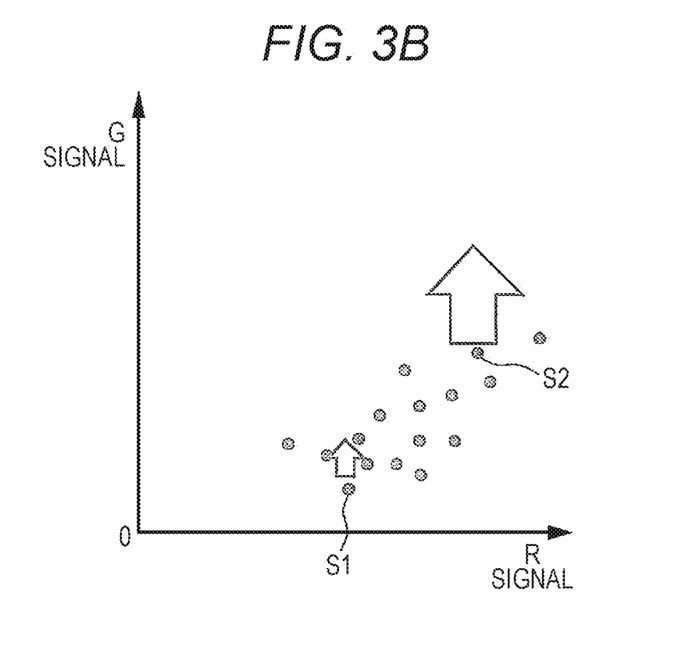

FIGS. 3A and 3B are diagrams illustrating an example of enhancement processing performed by the processor 2 of the electronic endoscope system 1 of the present embodiment. FIG. 3A illustrates the ratio used for enhancement processing. In the example illustrated in FIG. 3A, the feature amount calculation unit 25A sets, in the color space formed by the R signal and the G signal, an origin of the color space, that is, the value of the R signal=the value of the G signal=0 as a reference value Sv, and uses this reference value Sv to calculate the ratio between the difference of the value of the R signal from the reference value Sv and the difference of the value of the G signal from the reference value Sv. The distribution of "*" in FIGS. 3(*a*) and 3(*h*) indicates distribution of R and G signals at pixels in the image. The ratio of a pixel S1 illustrated in FIG. 3A is small, while the ratio of a pixel S2 is large. An image of a living tissue includes a large number of pixels with high reddishness and basically large R signal value, whereas portions to be enhanced such as a lesion or a blood vessel in a living tissue include relatively low amount of G component and B component than other parts. Accordingly, the feature amount calculation unit 25A enlarges the increase amount of the G signal or B signal values in the pixels having the large ratio, and reduces the increase amount of the G signal or B signal values in the pixels having the small ratio so as to adjust signal values to widen the difference between the values of the G signal and the B signal, between the pixels having different G signal or B signal values. This adjustment makes it possible to distinguishably enhance the image of a portion where the number of shades in the G component and the B component is small, which has caused a lossy image.

In order to perform such enhancement processing, the feature amount calculation unit 25A calculates the ratio between the differences of the values of the two color signals from the reference value Sv. This ratio can be defined as an indicator of the feature amount of living tissue. The difference in the ratio indicates the difference in the color component characteristic corresponding to the color signal. Accordingly, pixels having a small ratio including a portion to be enhanced in a living tissue, such as a lesion or a blood vessel, can be defined as a characteristic portion that can be distinguished from the other pixels. Therefore, in order to create an image in which the characteristic portion can be distinguished, it is preferable to enhance this characteristic portion so as to stand out from the other portions. For the portions in which the G component or B component is relatively low compared to other portions, such as a lesion or blood vessel in a living tissue, reducing the increase amount in the G signal or B signal value compared to other portions would make the portion in the image more noticeable with respect to the other portions. In this manner, characteristic portions such as a lesion or a blood vessel in a living tissue can be distinguishably enhanced.

The image enhancement processing unit 25B determines the degree of increase or decrease of at least one of the values of the two color signals on the basis of the ratio calculated by the feature amount calculation unit 25A to perform image enhancement processing.

In the example illustrated in FIG. 3B, the G signal is adjusted such that the larger the calculated ratio, the larger the increase amount. There is no particular limitation on how to increase the value of the signal.

According to one embodiment, a result of multiplying the ratio by a constant coefficient is added to the value of the G signal to obtain an adjusted value. According to one embodiment, a result of multiplying the ratio by a constant coefficient is multiplied to the value of the G signal to obtain an adjusted value. According to one embodiment, a value when a result obtained by multiplying the above ratio by a constant coefficient is to be used as an exponent, for example, a value $a^x$ having an exponent being x and a base being a, is multiplied by the value of the G signal, and then the multiplied value is to be used as an adjusted value. According to one embodiment, the output value is calculated using a functional expression that returns a larger output value together with an increase in the ratio, and a value obtained by multiplying this output value by the value of the G signal is to be used as an adjusted signal value.

In the example illustrated in FIG. 3B, the larger ratio the pixel has, the larger the image enhancement processing unit 25B adjusts the value of the color signal to. For this reason, even when the value of the Ci signal is small, a portion where the value of the G signal is relatively larger than the value of the R signal (portion having a large ratio) is enhanced to have a larger value.

Since conventional methods uniformly enhance middle shade levels in many cases, it has been difficult to perform enhancement processing for a specific color in a dark part even when a portion to be enhanced exists in a part darker than the middle shade level in the image. The present embodiment, however, the degree of enhancement is set on the basis of the ratio even in a dark part, making it possible to perform enhancement processing even in the dark part.

The ratio is a ratio of a second difference of a value of the second color signal from the reference value Sv corresponding to the second color signal with respect to a first difference of a value of the first color signal from the reference value Sv corresponding to the first color signal, out of two color signals of each of pixels. The greater the ratio, the more the image enhancement processing unit 25B enlarges the increase amount of the value of the second color signal. Alternatively, however, according to one embodiment, it would be also preferable that the image enhancement processing unit 25B enlarges the decrease amount of the value of the first color signal while maintaining the value of the second color signal or enlarging the increase amount of the value of the second color signal. Such processing widens, in a processed portion, the difference in the values of the first color signal to enhance the change in the tint of the pixel, making it possible to achieve the enhancement of this portion.

Note that, as described above, portions to be enhanced such as a lesion or a blood vessel in a living tissue have less G components and B components than other portions. Accordingly, the G signals and B signals are adjusted to have a relatively greater difference between large and small signal values relative to the R signals, thereby making it possible to distinguishably enhance the image of the portion of the G component or the B component having a small number of shades and thus having been a lossy image. Therefore, in a case where the color signal is RGB color signals in an image of a living tissue, it is preferable that the ratio to be used in enhancement processing includes at least one of a ratio of a difference of a value of the G signal from the reference value Sv corresponding to the G signal with respect to a difference of a value of the R signal from the reference value Sv corresponding to the R signal, or a ratio of a difference of a value of the B signal from the reference value Sv corresponding to the B signal with respect to a difference of the value of the R signal from the reference value Sv corresponding to the R signal, out of the RGB color signals.

Figure 4:
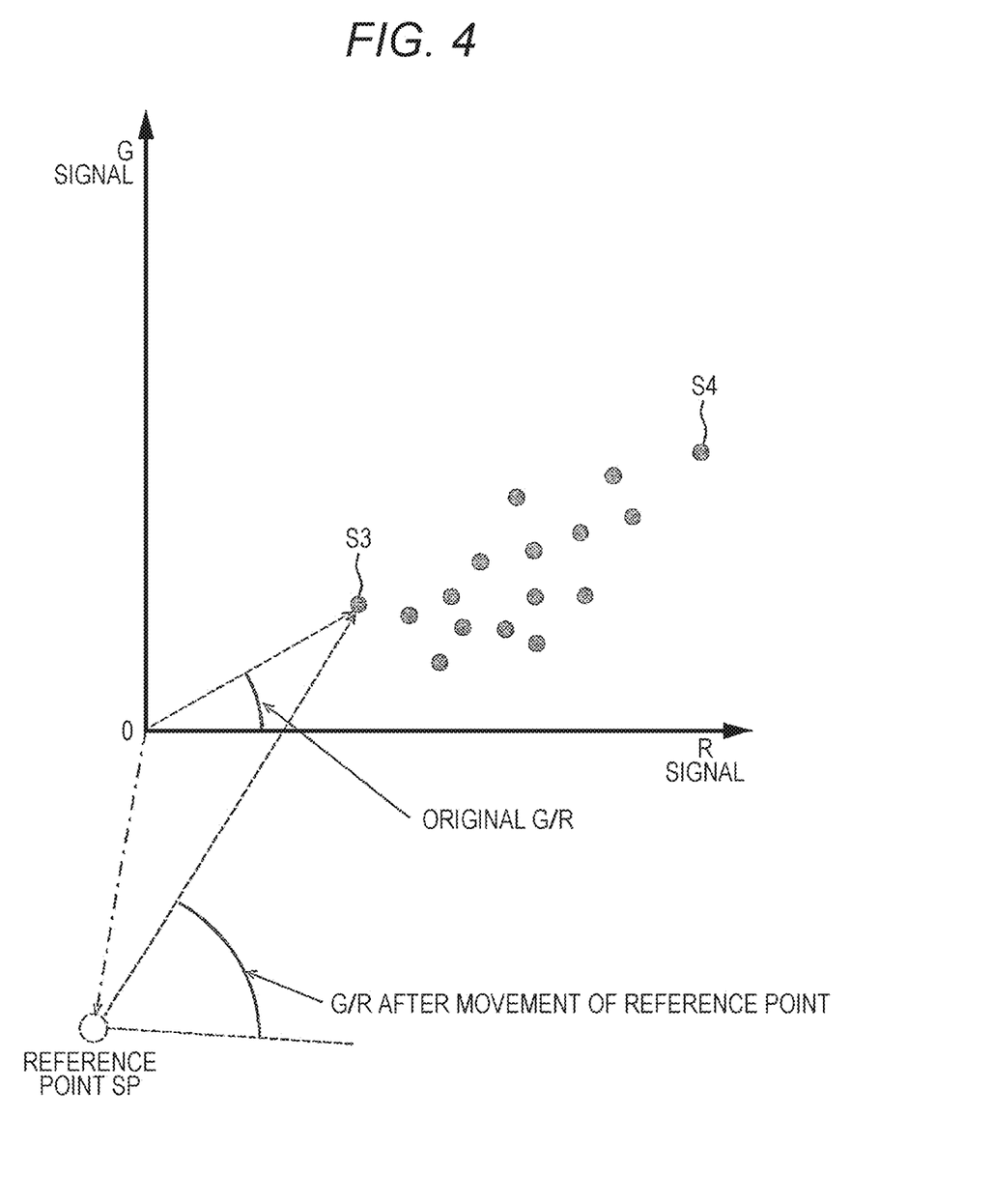
FIG. 4 is a diagram illustrating another example of enhancement processing performed by the electronic endoscope system of the present embodiment.

Furthermore, according to one embodiment, the reference value Sv used to calculate the ratio includes a first reference value for the first color signal and a second reference value for the second color signal. At this time, each of the first reference value and the second reference value is preferably a changeable value. That is, in the example illustrated in FIG. 3A the value of the origin (value of R signal=value of G signal=0) in the color space of two color signals (R signal and G signal) is defined as the reference value Sv. However, as illustrated in FIG. 4, the feature amount calculation unit 25A is preferably capable of changing each of the first reference value corresponding to the first color signal and the second reference value corresponding to the second color signal. For example, a point moved from the origin O so as to be away from or closer to the distribution of pixels in the color space is defined as a reference point Sp, and a coordinate position of the first color signal of the reference point Sp and a coordinate position of the second color signal of the reference point Sp are defined as a first reference value and a second reference value, respectively. In a case where the reference point Sp is located at a position moved away from the distribution of pixels with respect to the origin O, the change in the ratio at each of pixels is small, leading to a low degree of image enhancement processing between pixels. In contrast, in a case where the reference point Sp is located at a position moved to be closer to the distribution of pixels with respect to the origin O, the change in the ratio at each of pixels is large, leading to a high degree of image enhancement processing between pixels, meaning hi contrast in the image. Moving the reference point Sp so as to be closer to the distribution of pixels would be effective in changing the degree of enhancement processing in accordance with feature amount (ratio) of the pixel in an image with less brightness variation (image with uniform brightness). In this manner, since the first reference value and the second reference value are changeable, the degree of enhancement can be flexibly adjusted. The first reference value and the second reference value for such adjustment may be set to values input by an operator, or may be set automatically in accordance with the distribution, in the color space, of pixels in the image or the luminance information of the image. In a case where an operator inputs the first reference value and the second reference value, it is preferable to configure such that the operator temporarily inputs the first reference value and the second reference value manually while viewing an unprocessed still image displayed on the display 5, and that a processed image on which enhancement processing based on the first reference value and the second reference value has been performed is displayed every time the operator performs temporary input setting. In this case, it is preferable that the operator searches and sets optimal the first and second reference values by trial and error method while viewing the processed image.

According to one embodiment, when changing the reference value Sv, it is preferable that the feature amount calculation unit 25A sets change amounts of the first reference value and the second reference value to be different from each other. FIG. 4 is a diagram illustrating another example of enhancement processing, in which the reference point Sp has been moved from the origin O to a position in a negative coordinate axis direction of the G signal in the color space of the R and G signals.

In the example illustrated in FIG. 4, moving the reference point Sp from the origin O causes the change amount of the second reference value corresponding to the G signal to be larger than the change amount of the first reference value corresponding to the R signal. In addition, since the ratio of a pixel S3 having small R signal and G signal values is larger than the ratio of a pixel S4 having large R signal and G signal values. According, the increase amount in the G signal value for enhancement processing for the pixel S3 is larger than the increase amount in the G signal value for enhancement processing for the pixel S4. That is, the G component is higher in the pixel S3 and its peripheral pixels in a dark part than in the pixel S4 and its peripheral pixels in a bright portion. This leads to enhancement to widen the difference between the signal values in the pixel S3 and its peripheral pixels, making it possible to perform enhancement processing to change the image of the dark part to be distinguishable while brightening the dark part.

According to one embodiment, such movement of the reference point Sp is preferably performed in at least one of the color spaces, that is, the color space of the R signal and the G signal, or the color space of the R signal and the B signal.

In this manner, according to the enhancement processing on the image of the present embodiment, flexibly moving the reference point Sp in accordance with the color signal to be enhanced would make it possible to set the degree of contrast. In addition, an image existing present in a dark part and difficult to distinguish can be selectively brightened, and can be enhanced to become distinguishable.

According to one embodiment, the feature amount calculation unit 25A preferably sets the reference value Sv in accordance with the distribution of two color signals of whole of the image (distribution of pixels on the color space of R signal and G signal, or distribution of pixels on the color space of R signal and B signal), or in accordance with the luminance information of the whole of the image. For example, when the tint of the R component is high in the whole of the image (when the ratio of the number of pixels in which R signal value exceeds a predetermined threshold to the total number of pixels is a predetermined number or more), it is preferable, as illustrated in FIG. 4, to configure the feature amount calculation unit 25A to cause the reference point Sp to move automatically in order to adjust the degree of enhancement of the signal value and the B signal value with respect to the value of the R signal and distinguishably display the portion buried in the reddish image. In addition, in a case where a portion to be enhanced exists in a dark part where luminance information regarding the whole of the image, for example, the average luminance value of the image is lower than a predetermined value, the feature amount calculation unit 25A may preferably be configured to automatically move the reference point Sp in a predetermined direction by a predetermined distance in order to set the reference value Sv in accordance with the average luminance value. For example, due to the limitation of the spread of illumination light, an image obtained by imaging a living tissue in a large space in a human body tends to have a dark part formed in a region outside the central portion of the image. Images to be enhanced exist in such a dark part in some cases. Note that the luminance is represented by a linear sum of individual values of the R signal, the G signal, and the B signal.

(Flow of Image Enhancement Processing)

Figure 5:
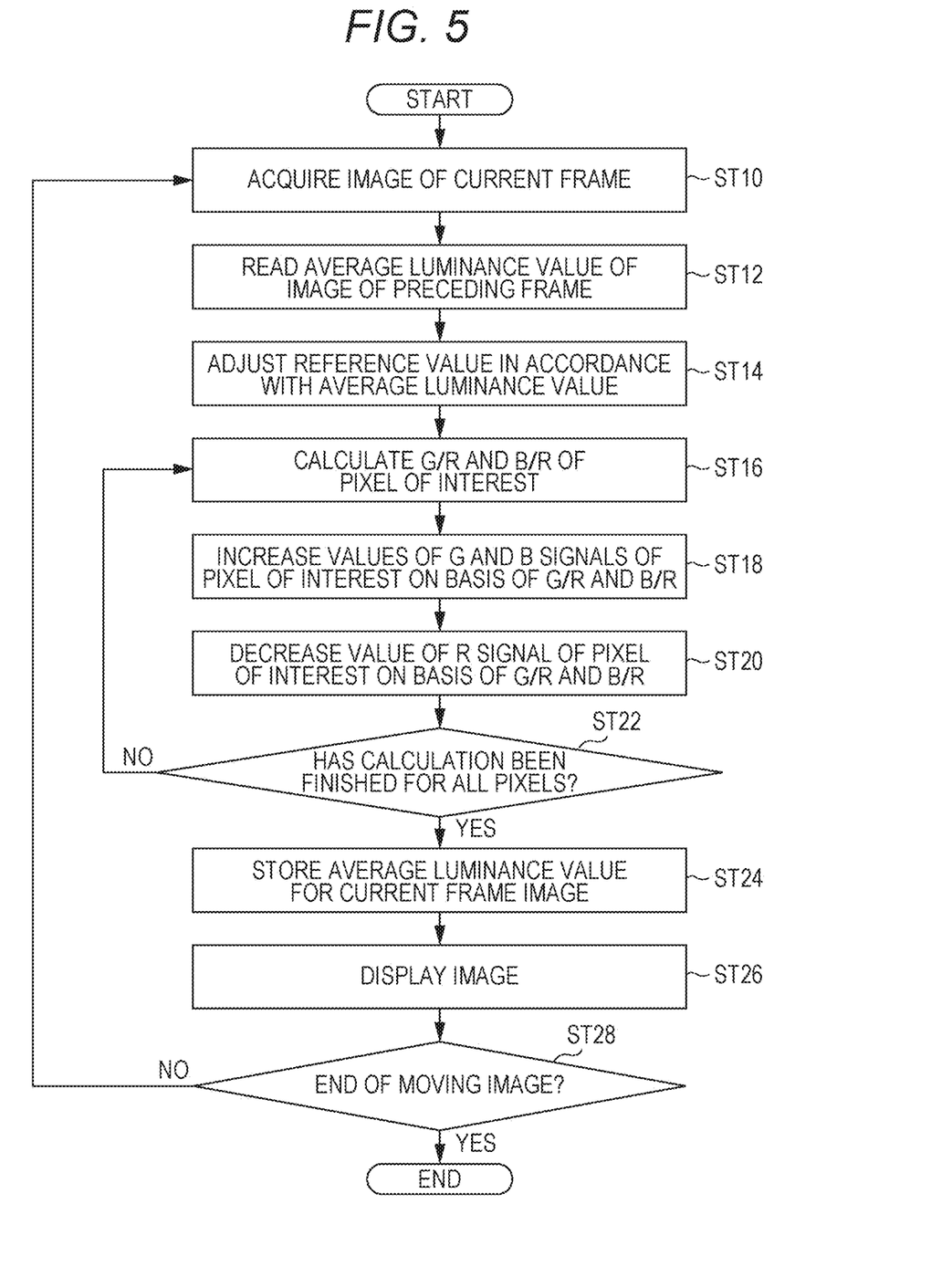
FIG. 5 is an example of a flow of enhancement processing performed by the electronic endoscope system of the present embodiment.

FIG. 5 is an example of a flow of enhancement processing performed by the electronic endoscope system 1. The example illustrated in FIG. 5 illustrates an example of enhancement processing performed on each of images in a moving image.

The feature amount calculation unit 25A acquires an image including the RGB signal of the current frame stored in the image memory 22 (step ST10).

After acquisition of the image, the feature amount calculation unit 25A reads a luminous average value of the image of the previous frame stored in the memory (step ST12). As described above, the feature amount calculation unit 25A uses the average luminance value to determine the position of the reference value Sv (reference point Sp) that determines the ratio, as described above. That is, the feature amount calculation unit 25A automatically adjusts the position of the reference point Sp (reference value Sv) in accordance with the average luminance value as illustrated in FIG. 4 (step ST14).

The feature amount calculation unit 25A defines each of pixels of an image as a pixel of interest, and calculates a feature amount of each of the pixel of interest. That is, the feature amount calculation unit 25A calculates a ratio G/R of a difference of a value of the G signal from the reference value Sv corresponding to the G signal with respect to a difference of a value of the R signal from the reference value Sv corresponding to the R signal, or a ratio B/R of a difference of a value of the B signal from the reference value Sv corresponding to the B signal with respect to a difference of the value of the R signal from the reference value Sv corresponding to the R signal (step ST16).

The image enhancement processing unit 25B determines the increase amount of the B signal and G signal values of the pixel of interest on the basis of the ratio G/R and the ratio B/R, and increases the G signal and B signal values (step ST18).

The image enhancement processing unit 25B determines the decrease amount of an R signal value of the pixel of interest on the basis of the ratio G/R and the ratio B/R, and decreases the R signal value (step ST20).

The image enhancement processing unit 25B determines whether the calculation has been completed for each of all the pixels in the image as the pixel of interest (step ST22). Arithmetic unit 25 repeats steps ST16 to ST20 until the calculation for all the pixels is completed.

When the calculation of all the pixels is completed, the feature amount calculation unit 25A calculates the average luminance value of the image before the enhancement processing in the current e and stores the calculated value in the memory (step ST24).

In this manner, in a case where the image on which the enhancement processing is performed is one image out of the moving image of the living tissue, the feature amount calculation unit 25A and the image enhancement processing unit 25B sequentially process each of the images of the moving image. At this time, the luminance information (average luminance value) used for setting the reference value Sv is preferably the luminance information (average luminance value) of the whole of a last image preceding before the image on which enhancement processing is performed in time series, out of the moving image. There is no great luminance change between images of consecutive frames in a moving image, and thus, effective utilization of the luminance information (average luminance value) of the image of the preceding frame makes it possible to set the value of the reference value Sv used for the enhancement processing in a short time.

The image on which enhancement processing has been performed in the arithmetic unit 25 is stored in the image memory 22 via the system controller 24. Thereafter, the result display unit 23 uses one lookup table and converts the value of each of pixels of the image into each of shade levels, and further converts the level into a signal for image display. A signal for image display is transmitted to the display 5. The display 5 displays the image on which enhancement processing has been performed as one frame image of a moving image (step ST26).

The arithmetic unit 25 determines whether the moving image has been finished (step ST28), and the arithmetic unit 25 repeats steps ST10 to ST28 until the moving image is finished.

In this manner, the arithmetic unit 25 of the processor 2 calculates the ratio of the differences between of the values of two color signals of the plurality of color signals of each of pixels of the image from the reference value Sv, determines a degree of increase or decrease (amount of increase or decrease) of at least one of the two color signal values on the basis of the calculated ratio, and thereby performs image enhancement processing. Therefore, it is possible to flexibly change the degree of enhancement processing on a characteristic portion having characteristic color components in the image and portions other than the characteristic portion without preparing a large number of lookup tables defining a tone curve as in conventional technologies. Therefore, even when a portion to be enhanced exists in a dark part of the image, enhancement processing can be performed on the corresponding portion while brightening the dark part.

Figure 6:
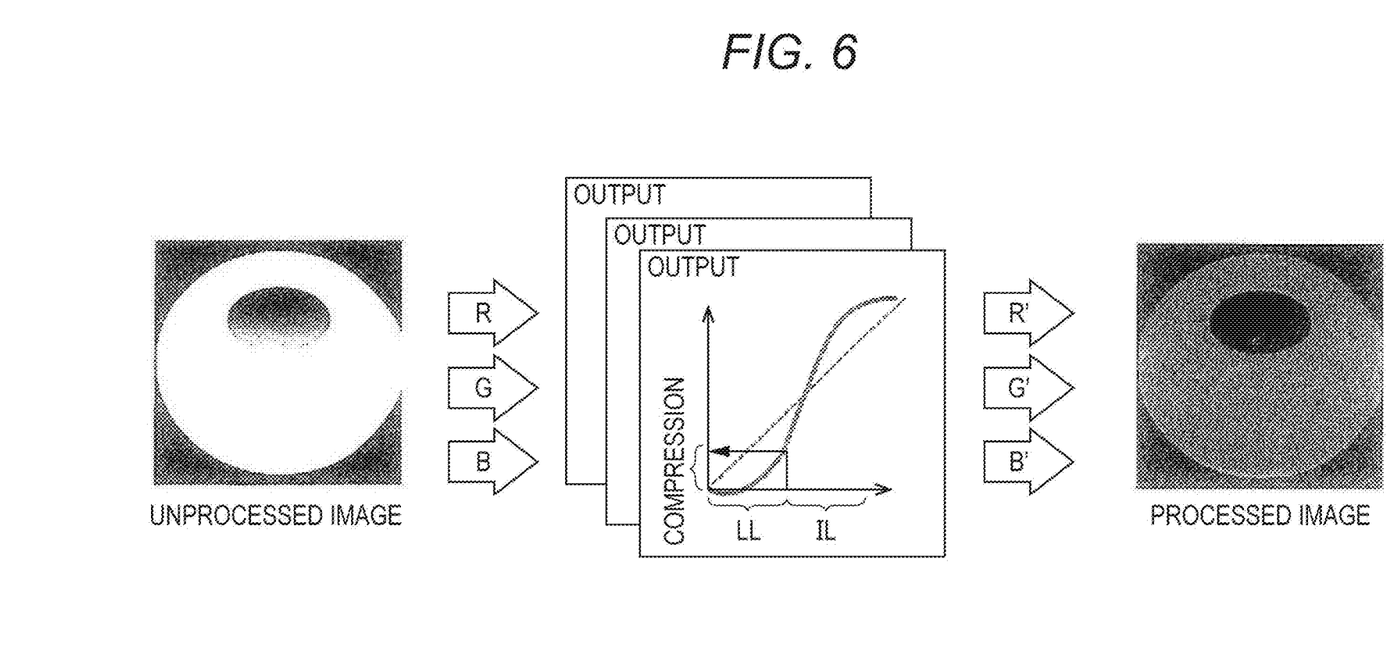
FIG. 6 is a diagram illustrating enhancement processing performed by a conventional electronic endoscope system.

FIG. 6 is a diagram illustrating enhancement processing performed by a conventional electronic endoscope system. In the example illustrated in FIG. 6, there is a characteristic portion to be enhanced in a dark part. However, since the enhancement processing for expanding a middle shade level IL is performed on the whole of the image, the number of shades in the dark part (low shade level LL) is reduced, leading to difficulty in distinguishing the characteristic portion to be enhanced. On the other hand, performing enhancement processing of increasing the number of shades of the low shade level LL on the whole of the image would reduce the number of shades in the bright part, which makes distinction difficult. Therefore, with the conventional enhancement processing, it is very difficult to perform processing of increasing the number of shades of the dark part (low shade level LL) while maintaining the distinction of the bright part. In other words, locally and selectively enhancing characteristic portions in the image would be very difficult by the conventional enhancement processing.

Figure 7:
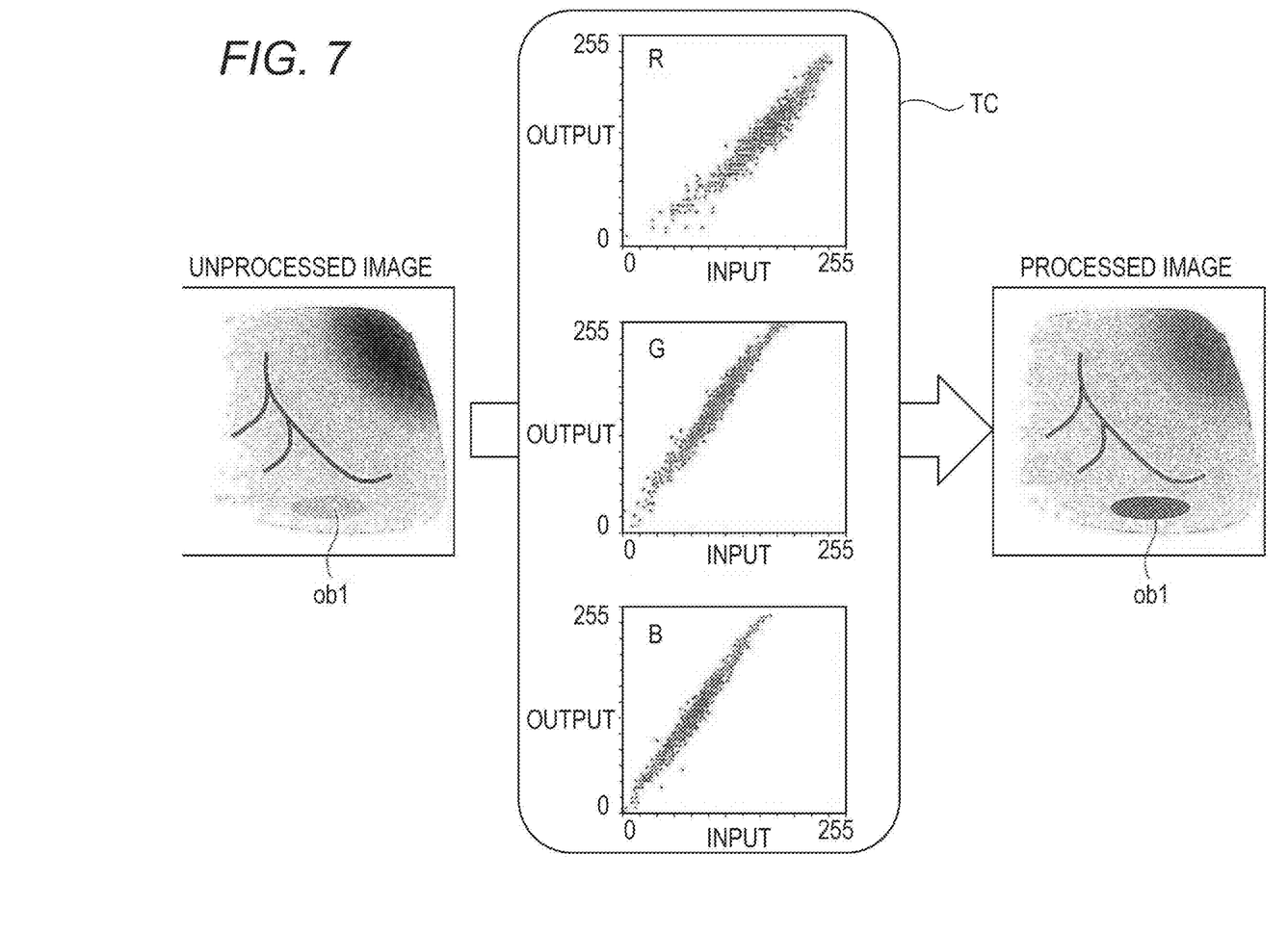
FIG. 7 is a diagram illustrating an example of a result of enhancement processing performed by the electronic endoscope system of the present embodiment.
Figure 8:
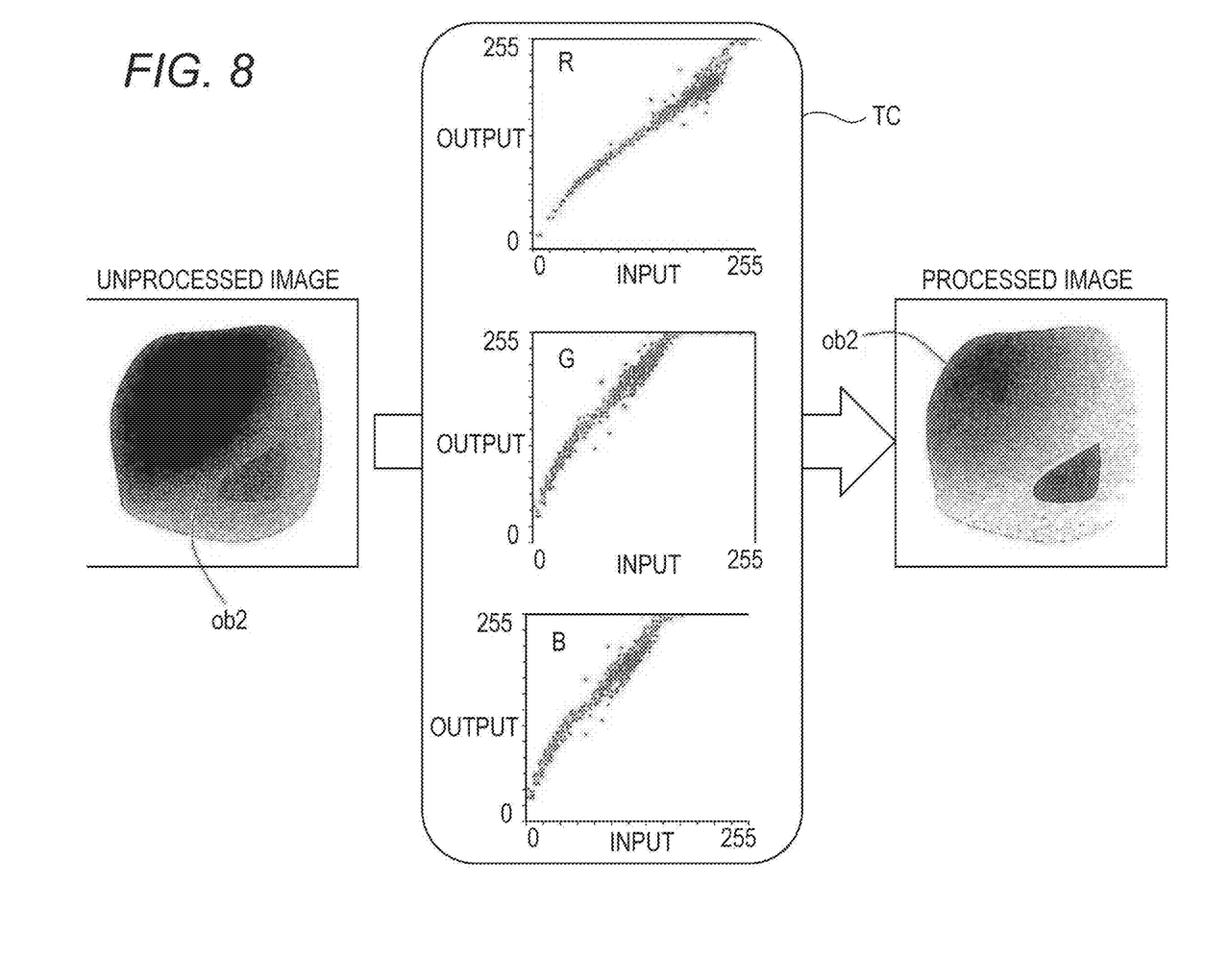
FIG. 8 is a diagram illustrating another example of a result of enhancement processing performed by the electronic endoscope system of the present embodiment.

FIGS. 7 and 8 are diagrams illustrating an example of a result of enhancement processing performed by the electronic endoscope system 1.

The example illustrated in FIG. 7 illustrates an example of a result of enhancement processing performed following the flow illustrated in FIG. 5 on an image having a portion Ob1 to be enhanced in the bright part of the image. In this case, the enhancement processing is performed with the reference point Sp set as the origin in the color space. The portion Ob1 in the bright part in the unprocessed image is reproduced as a part which can be more clearly distinguished by the enhancement processing in the processed image. The sign TC in FIG. 7 indicates a diagram illustrating an input-output relationship in the R signal, the G signal, and the B signal between the unprocessed image and the processed image. This input-output relationship corresponds to a conventional tone curve. In this manner, the input-output relationship of the enhancement processing of the present embodiment illustrated in FIG. 7 corresponds to processing results using various tone curves, rather than one tone curve. That is, the degree of the enhancing of enhancement processing is changed in accordance with the feature amount (ratio) of the pixel in the enhancement processing of the present embodiment illustrated in FIG. 7, and thus, this corresponds to the use of a plurality of different tone curves according to the feature amount in the image. The example illustrated in FIG. 7 is comparison between the output level in the input-output relationship of the R signal and the output level in the input-output relationship of the G signal and the B signal. This comparison indicates a state having a number of shades at low to middle shade levels of the R signal (reducing the number of shades for the input signal having shade levels in low to middle ranges and generating an output signal), and a state having relatively a large number of shades at low to middle shade levels of the G signal and B signal (increasing the number of shades for the input signal having shade levels in low to middle ranges and generating an output signal).

The example illustrated in FIG. 8 illustrates an example of a result of execution of enhancement processing illustrated in FIG. 5 on an image having a portion Ob2 to be enhanced in a dark part of the image. In this case, enhancement processing is performed in a state where the reference point Sp has been moved, with respect to the origin in the color space, to a point corresponding to a position having a shade level of −20 in the axial direction of the R signal is 256 when converted to the number of 256 shades of the R signal and having a shade level of −40 in the axial direction of the G signal in the number of 256 shades of the G signal. The portion Ob2 in the dark part in the unprocessed image becomes brighter and is reproduced as an enhanced portion that can be more clearly distinguished by the enhancement processing in the processed image. The sign TC in FIG. 8 indicates a diagram illustrating an input-output relationship in the R signal, the G signal, and the B signal between the unprocessed image and the processed image. This input-output relationship corresponds to a conventional tone curve. In this manner, the input-output relationship of the enhancement processing of the present embodiment illustrated in FIG. 8 corresponds to processing results using various tone curves, rather than one tone curve. That is, the enhancing of enhancement processing is changed in accordance with the feature amount (ratio) of the pixel in the enhancement processing of the present embodiment illustrated in FIG. 8, and thus, this corresponds to the use of a plurality of different tone curves according to the feature amount in the image. The example illustrated in FIG. 8 indicates a state where the number of shades of the low shade level is increased at the output level in the input-output relationship of each of the R signal, G signal and B signal so as to brighten the dark part and where the number of shades of the G signal and the B signal is increased more than the number of shades of the R signal in the low shade level.

The above has described the electronic endoscope system of the present technology in detail. The electronic endoscope system is not limited to the above-described embodiment, and may of course be modified or altered in various ways in a range not deviating from the scope and spirit of the present technology.

REFERENCE SIGNS LIST

1 Endoscope system
2 Processor
3 Light source device
4 Endoscope
5 Display
21 Image input processing unit
22 Image memory
23 Result display unit
24 System controller
25 Arithmetic unit
25A Feature amount calculation unit
25B Image enhancement processing unit
42 Insertion portion
44 Hand operation unit
45 Bending portion
46 Distal end portion
46A Objective lens
46B Image sensor
48 Light guide
49 Connector unit

The invention claimed is:

1. An electronic endoscope system comprising:
an electronic endoscope including an image sensor configured to image a living tissue;
a processor configured to perform image processing on an image obtained by imaging the living tissue; and
a display configured to display the image on which image processing has been performed,
the processor including:
a feature amount calculator configured to calculate, as a feature amount, a ratio between differences of values of two color signals out of a plurality of color signals of each of pixels of the image from respective reference values for the two color signals; and
an image enhancement processor configured to:
enhance the image by increasing the ratio for each of the pixels of the image by using an increase amount of the ratio, the increase amount being greater as the ratio is greater, the image enhancement processor further configured to determine, based on the increased ratio, a degree of increase or decrease of at least one of the values of the two color signals, and
adjust an enhancement level by adjusting a distance between a reference point defined by the reference values for the two color signals in a color space formed by the two color signals and a distribution of the two color signals of the pixels in the color space by moving the reference point, the distribution comprising a plurality of points each corresponding to the two color signals of one of the pixels in the color space.

2. The electronic endoscope system according to claim 1, wherein the two color signals are a first color signal and a second color signal,
the ratio is a ratio of a second difference of a value of the second color signal from one of the reference values corresponding to the second color signal with respect to a first difference of a value of the first color signal from one of the reference values corresponding to the first color signal, and
the image enhancement processor is configured to perform at least one of enlarging an increase amount of the value of the second color signal or enlarging a decrease amount of the value of the first color signal, as the ratio becomes greater.

3. The electronic endoscope system according to claim 2, wherein the reference values include a first reference value for the first color signal and a second reference value for the second color signal, and each of the first reference value and the second reference value is a changeable value.

4. The electronic endoscope system according to claim 3, wherein, when changing the reference values, the feature amount calculator is configured to set change amounts of the first reference value and the second reference value to be different from each other.

5. The electronic endoscope system according to claim 4, wherein the feature amount calculator is configured to adjust, before enhancing the image, the reference values used for calculating the ratio in accordance with distribution of the two color signals on whole of the image or luminance information regarding the whole of the image.

6. The electronic endoscope system according to claim 5, wherein the image is one image out of a moving image of a living tissue,
the feature amount calculator and the image enhancement processor are configured to process each of images of the moving image sequentially, and
the luminance information used for setting the reference values is luminance information of whole of a last image preceding before the image on which enhancement processing is performed in time series, out of the moving image.

7. The electronic endoscope system according to claim 1, wherein the feature amount calculator is configured to set the reference values to input values received from an operator viewing the image displayed on the display, and the image enhancement processor is configured to use the set reference values to perform enhancement processing on the image.

8. The electronic endoscope system according to claim 1, wherein the color signals are RGB color signals, and
the ratio includes one of a ratio of a difference of a value of a G signal from one of the reference values corresponding to the G signal with respect to a difference of a value of an R signal from one of the reference values corresponding to the R signal, or a ratio of a difference of a value of a B signal from one of the reference values corresponding to the B signal with respect to the difference of the value of the R signal from one of the reference values corresponding to the R signal.

9. The electronic endoscope system according to claim 1, wherein at least one of the reference values is other than zero.

10. The electronic endoscope system according to claim 1, wherein:

the two color signals are a first color signal and a second color signal, and the reference values include a first reference value for the first color signal and a second reference value for the second color signal, the first reference value and the second reference value being different each other.

11. The electronic endoscope system according to claim 1, wherein:

the two color signals are a first color signal and a second color signal, the reference values include a first reference value for the first color signal and a second reference value for the second color signal, each of the first reference value and the second reference value being a changeable value, and a change amount of the first reference value and a change amount of the second reference value are different each other when the first reference value and the second reference value are changed.

* * * * *